United States Patent [19]

Noguera et al.

[11] Patent Number: 4,959,206
[45] Date of Patent: Sep. 25, 1990

[54] PEARLING AGENT DISPERSION

[75] Inventors: Angel R. Noguera, Barcelona; Carlos C. Planells, Sant Cugat del valles; Masaki Itabashi, Barcelona, all of Spain

[73] Assignee: KAO Corporation, Tokyo, Japan

[21] Appl. No.: 289,251

[22] Filed: Dec. 23, 1988

[30] Foreign Application Priority Data

Dec. 28, 1987 [JP] Japan .................. 62-332792

[51] Int. Cl.$^5$ .................. A61K 7/06; B01J 13/00
[52] U.S. Cl. ...................... 424/70; 514/772; 514/785; 514/788; 252/DIG. 13; 252/308
[58] Field of Search ............... 424/70; 252/DIG. 13, 252/308; 514/785, 788, 772, 937

[56] References Cited

U.S. PATENT DOCUMENTS 4,620,976 11/1986 Quack et al. .

OTHER PUBLICATIONS

Sulfosuccinates in Shampoo Formulations, Soap & Chemical Specialties, Apr. 1967, pp. 178 and 180.

*Primary Examiner*—Merrell C. Cashion, Jr.
*Assistant Examiner*—Susan S. Rucker
*Attorney, Agent, or Firm*—Oblon, Spivak, McClelland, Maier & Neustadt

[57] ABSTRACT

A high-concentration pearling agent dispersion is disclosed. The dispersion comprises as essential components, at a specific proportion, a fatty acid glycolic ester of formula (I):

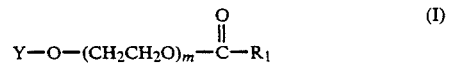

wherein $R_1$ represents a linear or branched, saturated or unsaturated hydrocarbon group of a $C_{13-21}$ carbon atom content, Y represents a hydrogen atom or a

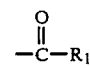

group, m indicates a value of 1 to 3, which is the average number of ethylene oxide group addition moles; an alkylsulfosuccinate or a polyoxyalkylenealkylsulfosuccinate of formula (II):

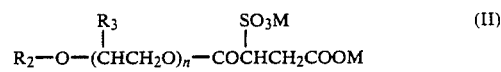

wherein $R_2$ represents a linear or branched alkyl group of a $C_{8-20}$ carbon atom content, $R_3$ represents a hydrogen atom or a methyl group, M represents an alkali metal, an alkali earth metal, an ammonium ion, an alkyl group-substituted ammonium with the alkyl group having a $C_{1-3}$ carbon atom content, or a hydroxy alkyl group-substituted ammonium with the hydroxy alkyl group having a $C_{2-3}$ carbon atom content, n indicates a value of 0 to 8, which is the average number of addition moles; a fatty acid dialkanol amide of formula (III):

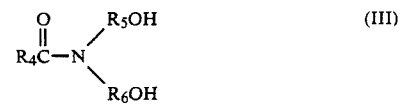

wherein $R_4$ represents a linear or branched, saturated or unsaturated hydrocarbon goup of a $C_{7-17}$ carbon atom content, and $R_5$ and $R_6$ independently represent a group —$C_2H_4$ or —$C_3H_6$; and water. The pearling agent dispersion comprises uniformly shaped crystals, has a low viscosity, and exhibits a superior stability at high and low temperatures.

4 Claims, 1 Drawing Sheet

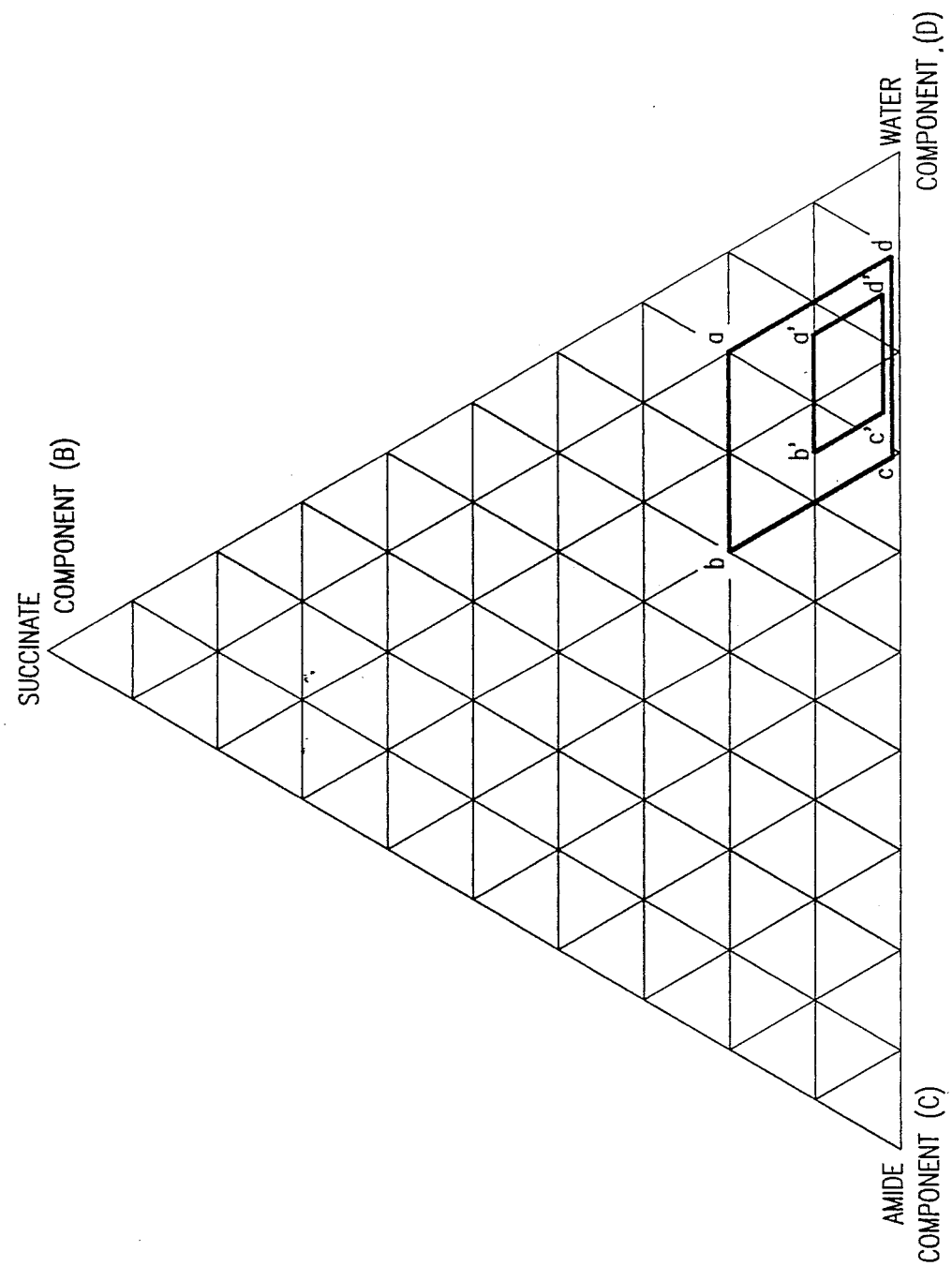

PEARLING AGENT DISPERSION

BACKGROUND OF THE INVENTION

1. Field of the Invention:

This invention relates to a high-concentration pearling agent dispersion, and, more particularly, to a high-concentration pearling agent dispersion prepared by mixing a large amount of a fatty acid glycolic ester with specific types of solvent, heating the mixture, and then cooling it to deposit crystals of the fatty acid glycolic ester. The pearling agent dispersion comprises uniformly shaped crystals, has a low viscosity, and exhibits a superior stability at high and low temperatures.

2. Description of the Background:

Pearl-like gloss is often given to such compositions as shampoos, rinses, hair-washing creams, and liquid detergents in order to enhance their commercial value. One of the conventional methods of providing pearl-like gloss to such a composition is to mix it with a pulverized natural substance or an inorganic compound such as mica, fish scale, bismuth oxychloride, or the like. Another method is to crystallize a polyvalent metal salt of a higher fatty acid or a fatty acid glycolic ester.

Among these the method using a fatty acid glycolic ester is generally accepted in recent years. In this method a fatty acid glycolic ester which is solid at room temperature is added to a composition such as shampoo or the like, followed by heating of the mixture to melt the fatty acid glycolic ester, and then by cooling to recrystallize it, thereby providing pearl-like gloss to the composition. Alternatively, a pearling agent dispersion, e.g. a fatty acid glycolic ester dispersion, which is dissolved and cooled to recrystallize in advance, is mixed with a shampoo or the like at room temperature (Japanese Pat. Publication No. 804/1972, Japanese Pat. Application Laid-open Nos. 71021/1981, 216728/1983, etc.).

The method proposed by Japanese Pat. Publication No. 804/1972 is to employ a fatty acid glycolic ester together with a fatty acid dialkanol amide to induce pearl-like gloss. According to this method, however, if the pearling agent component is used at a high concentration the mixture becomes unreasonably viscous so that difficulty is encountered in handling it in the course of preparing a shampoo composition or the like at room temperature. In addition, it takes a long period of time to mix it homogeneously with other components.

Japanese Pat. Application Laid-open No. 71021/1981 discloses a method for preparing a pearling agent containing a fatty acid glycolic ester at a high concentration. This method, however, only provides a pearling agent with fatty acid glycolic ester crystals having varied crystal sizes and non-uniform crystal shapes. Thus, according to this method it is very difficult to produce a pearling agent providing a beautiful outward appearance.

Japanese Pat. Application Laid-open No. 216728/1983 discloses a pearling agent containing a salt of alkyl sulfate or a salt of polyoxyalkylene alkyl sulfate, a fatty acid dialkanol amide and water, as solvents, and a fatty acid glycolic ester at a high concentration. Alkyl sulfates contained in this pearling agent, however, have the drawback of producing a strong irritation to the skin. Use of an alkylether sulfate instead of an alkyl sulfate reduces irritation to the skin. In their manufacturing processes alkylether sulfates, however, are inevitably contaminated by dioxane, which is a potentially hazardous material.

In view of this situation, the present inventors have undertaken extensive studies for developing a high concentration pearling agent which is free from these drawbacks existing in the conventional pearling agents. As a result, the inventors have found that the use of an alkylsulfosuccinate or a polyoxyalkylenealkylsulfosuccinate, a fatty acid dialkanol amide, and water, together as solvents, mixed at a certain proportion with a fatty acid glycolic ester provides a high concentration, low viscosity pearling agent, which is less of an irritant, has crystals of a uniform shape, is stable at high and low temperatures, and provides a beautiful outward appearance. This finding has led to the completion of this invention.

SUMMARY OF THE INVENTION

Accordingly, an object of this invention is to provide a pearling agent dispersion comprising as essential components:

(A) 10 to 40% by weight of a fatty acid glycolic ester represented by the following formula (I):

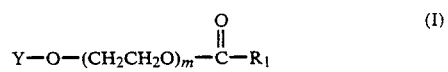

wherein $R_1$ represents a linear or branched, saturated or unsaturated hydrocarbon group of a $C_{13-21}$ carbon atom content, Y represents a hydrogen atom or a

group, m indicates a value of 1 to 3, which is the average number of ethylene oxide group addition moles, (B) 0.8 to 16% by weight of an alkylsulfosuccinate or a polyoxyalkylenealkylsulfosuccinate represented by the following formula (II):

wherein $R_2$ represents a linear or branched alkyl group of a $C_{8-20}$ carbon atom content, R3 represents a hydrogen atom or a methyl group, M represents an alkali metal, an alkali earth metal, an ammonium ion, an alkyl group-substituted ammonium with the alkyl group having a $C_{1-3}$ carbon atom content, or a hydroxy alkyl group-substituted ammonium with the hydroxy alkyl group having a $C_{2-3}$ carbon atom content, n indicates a value of 0 to 8, which is the average number of addition moles, (C) 8 to 24% by weight of a fatty acid dialkanol amide of the following formula (III):

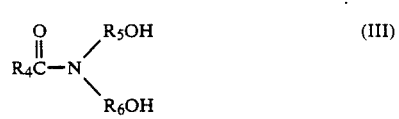

wherein $R_4$ represents a linear or branched, saturated or unsaturated hydrocarbon group of a $C_{7-17}$ carbon atom content, and $R_5$ and $R_6$ independently represent a group $-C_2H_4$ or $-C_3H_6$, and (D) 50 to 81% by weight of water; and wherein the ratio of the components (B), (C), and (D) lies within a region encircled by straight lines linking the following four points of a three-component trigonometric diagram:

a [(B)=20 : (C)=10 : (D)=70],
b [(B)=20 : (C)=30 : (D)=50],
c [(B)=1 : (C)=30 : (D)=69], and
d [(B)=1 : (C)=10 : (D)=89].

Other objects, features and advantages of the invention will hereinafter become more readily apparent from the following description.

BRIEF DESCRIPTION OF THE DRAWINGS

FIG. 1 is a three-component trigonometric diagram showing the ratio of the three components used in the pearling agent dispersion of this invention.

DETAILED DESCRIPTION OF THE INVENTION AND PREFERRED EMBODIMENTS

Among fatty acid glycolic esters, component (A), represented by formula (I), those having a carbon atom content of $C_{15-17}$ for $R_1$ are particularly preferable because of their remarkably beautiful pearl-like gloss. Fatty acid glycolic esters having average addition moles of ethyleneoxide, i.e, the value for m in formula (I), of 3, exhibit an excellent pearl-like gloss, even though the carbon atom content for $R_1$ is $C_{19-21}$. Also, those having a

group for Y in formula (I) are preferable. One or more compounds represented by formula (I) are formulated, as a component (A), into the pearling agent dispersion of the present invention in an amount of 10 to 40% by weight, and preferably of 20 to 30% by weight.

Given as preferable alkylsulfosuccinates or polyoxyalkylenealkylsulfosuccinates, component (B), represented by formula (II), are those having a linear or branched saturated hydrocarbon group of a $C_{10-14}$ carbon atom content in average for $R_2$ in formula (II). Alcohols either derived from natural sources or artificially synthesized can be used as raw alcohols for preparing the (B) component. As the (B) component having oxyalkylene groups, those having an oxyalkylene group derived from ethylene oxide are preferable. Given as counter ions for these alkyl sulfates are alkali metal ions such as sodium, potassium, or the like; alkali earth metal ions such as calcium, magnesium, or the like; ammonium ions; ammonium substituted with 1 to 2 hydroxy alkyl groups of a $C_{2-3}$ carbon atom content, e.g. groups derived from monoethanolamine, diethanolamine, triisopropanolamine, or the like. Particularly preferable counter ions are sodium ion, ammonium ion, triethanolamine, and the like. The (B) component is formulated into the pearling agent dispersion of the present invention in an amount of 0.8 to 16% by weight, and preferably 1.6 to 8% by weight. If the amount is less than 0.8% by weight, crystals of the pearling agent in the dispersion are not uniform, diminishing the beautiful pearl-like gloss of the dispersion. If the amount exceeds 16% by weight, the viscosity of the dispersion becomes too high to handle with ease.

Preferable fatty acid dialkanol amides, component (C) of the present invention, which are represented by formula (III), are those derived from raw fatty acids having a $C_{8-18}$ carbon atom content distribution. A particularly preferable fatty acid raw material is that having a lauric acid ($C_{12}$) content of greater than 40% by weight. Diethanolamine or diisopropanolamine is preferable as a raw alkanol amine for preparing a fatty acid dialkanol amide, with an especially ideal raw material being diethanolamine. The (C) component is formulated into the pearling agent dispersion of the present invention in an amount of 8 to 24% by weight, and preferably 10.4 to 20% by weight. If the amount is less than 8% by weight, fatty acid glycolic esters, component (A) cannot be sufficiently dispersed into the composition. If the amount exceeds 24% by weight, on the other hand, the viscosity of the dispersion becomes too high and crystals of the pearling agent in the dispersion are not uniform, diminishing the beautiful pearl-like gloss of the dispersion.

There are no specific limitations as to the type of water which is the (D) component of the present invention. Portable water, deionized water, purified water, or the like can be used.

It is essential in this invention that the ratio of the components (B), (C), and (D) lie within a region encircled by straight lines linking the following four points in a three-component trigonometric diagram: a [(B)=20 : (C)=10 : (D)=70], b [(B)=20 : (C)=30 : (D)=50], c [(B)=1 : (C)=30 : (D)=69], and d [(B)=1 : (C)=10 : (D)=89]. A more preferable range in terms of a three-component trigonometric diagram, however, is a region encircled by straight lines linking the points: a' [(B)=10 : (C)=13 : (D)=77], b' [(B)=10 : (C)=25 : (D)=65], c' [(B)=2 : (C)=25 : (D)=73], and d' [(B)=2 : (C)=13 : (D)=85].

The pearling agent dispersion of this invention can be prepared by a process in which each prescribed amount of the components (A), (B), (C), and (D) is charged into a vessel, heated, and stirred. In this process the mixture is heated to a temperature above the melting point of the (A) component, preferably to about 80° C. No specific limitations are imposed on a speed of the stirring. Low-speed stirring, for instance, of a 10 to 100 rpm range is usually sufficient. There are also no specific limitations as to the duration for which the mixture is to be stirred during heating. In view of the actual operation and workability, a stirring for a period of 5 to 60 minutes, preferably 20 to 40 minutes, is applicable. In one embodiment of the process for preparing the pearling agent dispersion of this invention, when the above components are heated to 80° C. and the mixture is stirred at this temperature for about 30 minutes, the (A) component melts and the mixture emulsified. The emulsion is then gradually cooled while stirring to an ultimate temperature of 10° to 40° C., preferably of 20° to 30° C. There are no specific limitations as to the method of cooling. It may be either gradual or rapid. The (A) component crystallizes at 50° to 60° C. and the whole liquid presents a beautiful pearl-like gloss, thus producing a pearling agent dispersion. Besides the above essential components (A), (B), (C), and (D), other components, including, for example, pH adjusting agents, antiseptics, and the like, can be formulated into the pearling agent dispersion of this invention, as required. It is preferable to adjust the pH of the dispersion to a range of 4 to 11, and, in particular, of 7 to 10. The pearling agent dispersion of this invention thus prepared can be formulated into a variety of compositions, including liquid shampoos, liquid detergent compositions, liquid rinse, or other similar liquid compositions, or into paste-like compositions, in an amount appropriate to the intended use of such compositions, thereby providing a beautiful pearl-like gloss to the compositions. In the case of a liquid-type composition the amount of the pearling agent dispersion to be formulated may be 1 to 20% by weight, and preferably 2 to 10% by weight.

Since the pearling agent dispersion of this invention contains very fine crystals of the pearling agent component of a size between 1 and 10 $\mu$, it is more homogeneous and presents a more beautiful pearl-like gloss than conventional molten-type pearling agents which comprise crystals having a size greater than about 30$\mu$. Furthermore, since in the pearling agent dispersion of this invention the viscosity increase is not remarkable, it can be prepared as a high concentration dispersion directed to formulation into a variety of other compositions.

In addition, since the pearling agent dispersion of this invention only weakly irritates the skin, it can have a wide variety of applications without being limited to use in liquid shampoos, liquid detergents, and the like.

Other features of the invention will become apparent in the course of the following description of the exemplary embodiments which are given for illustration of the invention and are not intended to be limiting thereof.

EXAMPLES

The invention is hereafter described in more detail by way of examples, which, however, shall not be construed as limiting the invention. In the examples below the following test methods were used.

(1) Appearance

A sample placed in a 100-ml transparent glass container was observed by the naked eye to investigate its pearl-like gloss. Any samples containing foam were subjected to centrifugation to eliminate the foam. The evaluation was performed according to the following standard:

O: The sample exhibited homogeneous pearl-like gloss.
X: The sample was turbid or emulsion-like, or its pearl-like gloss was not homogeneous.

(2) Viscosity

The same sample as used in the test (1) above was placed in a thermostat at a temperature of 30° C. and was maintained at this temperature, followed by measuring the viscosity using a B-type viscosimeter (manufactured by Tokyo Keiki Co., Ltd.).

(3) Stability at a high temperature

A sample was placed in a transparent glass container, sealed, and stored in a thermostat at a temperature of 50° C. for one month. The absence or presence of separation of the sample components and of agglomeration of the pearling agent was observed by the naked eye. The evaluation was performed according to the following standard:

O: No extraordinary phenomenon such as separation of the sample components, agglomeration of the pearling agent, or disappearance of the pearl-like gloss was observed.
X: Either of the extraordinary phenomena; separation of the sample components, agglomeration of the pearling agent, or disappearance of the pearl-like gloss was observed.

(4) Stability at a low temperature

A sample was placed in a transparent glass container, sealed, and stored in a thermostat at a temperature of −5° C. for one month. The absence or presence of separation or solidification of the sample components was observed by the naked eye. The evaluation was performed according to the following standard:

O: No separation or solidification of the sample components occurred and the fluidity of the sample was maintained.
X: An extraordinary phenomenon, including separation or solidification of the sample components, was observed.

EXAMPLE 1

(Composition No. 1)

| [Formulation] | |
| --- | --- |
| Distearic acid ethylene glycol | 20 parts by weight |
| Sodium polyoxyethylene (3) Laurylsulfosuccinate | 5 parts by weight |
| Coconut oil diethanol amide | 12 parts by weight |
| Water | 63 parts by weight |

[Preparation]

The above components were mixed while heating at 80° C. to melt the distearic acid ethylene glycol. The mixture was not transparent, but emulsion-like at this point of time. This mixture was cooled to 30° C. over 2 hours to produce a pearling agent dispersion in which a pearling agent having a uniform particle size was dispersed and which presented a beautiful outward appearance.

The dispersion thus prepared had a viscosity of 1,820 cp at 30° C.

COMPARATIVE EXAMPLE

Composition No. 2 (Comparative Composition)

| [Formulation] | |
| --- | --- |
| Distearic acid ethylene glycol | 20 parts by weight |
| Sodium polyoxyethylene (3) Laurylsulfosuccinate | 4 parts by weight |
| Coconut oil diethanol amide | 24 parts by weight |
| Water | 52 parts by weight |

[Preparation]

The above components were mixed while heating at 80° C. t melt the distearic acid ethylene glycol to produce a transparent material. This material was cooled to as low as 30° C., at which temperature the mixture exhibited a pearl-like gloss, but the particle size of the pearling agent crystals was not uniform and the outward appearance of the mixture was not beautiful.

The dispersion thus prepared was barely fluid with an apparent viscosity of 53,500 cp at 30° C.

EXAMPLE 2

The high-concentration pearling agent dispersion compositions listed in Table 1 were prepared using the components shown in the same table at various proportions in the same manner as in Example 1 or the Comparative Example. These compositions were evaluated according to the methods previously discussed. The results are shown in Table 1.

TABLE 1

| Dispersion Composition No. | 3 | 4 | 5 | 6 | 7 | 8 | 9 | 10 |
|---|---|---|---|---|---|---|---|---|
| Distearic acid ethylene glycol [Component (A)] (wt. %) | 20 | 20 | 20 | 20 | 20 | 20 | 20 | 20 |
| Solvent [(B) + (C) + (D)] (wt. %) | 80 | 80 | 80 | 80 | 80 | 80 | 80 | 80 |
| Ratio of Solvent (parts by weight) | | | | | | | | |
| Sodium polyoxyethylene (3) laurylsulfosuccinate (B) | 12.5 | 17 | 25 | 33 | 12.5 | 2 | 2.5 | 5 |
| Coconut oil fatty acid diethanol amide (C) | 4 | 10 | 10 | 2 | 25 | 25 | 15 | 15 |
| Water (D) | 83.5 | 73 | 65 | 65 | 62.5 | 73 | 82.5 | 80 |
| Viscosity (cp) | — | 880 | 80500 | — | 7400 | 5540 | 2730 | 1930 |
| Appearance | X | X | X | X | X | O | O | O |
| High-temperature stability | X | X | O | X | O | X | O | O |
| Low-temperature stability | X | X | O | X | O | X | O | O |

As was evidenced from the results of Example 1 and the Comparative Example, and from the results shown in Table 1, a pearling agent dispersion exhibiting satisfactory performance can be obtained only when the ratio of the components (B), (C), and (D) is in a range encircled by straight lines linking the four points a, b, c, and d together as in FIG. 1.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. A pearling agent dispersion comprising as essential components:
   (A) 10 to 40% by weight of a fatty acid glycolic ester represented by the following formula (I):

$$Y-O-(CH_2CH_2O)_m-\overset{O}{\underset{\|}{C}}-R_1 \qquad (I)$$

wherein $R_1$ represents a linear or branched, saturated or unsaturated hydrocarbon group of a $C_{13-21}$ carbon atom content, Y represents a hydrogen atom or a $$-\overset{O}{\underset{\|}{C}}-R_1$$

group, m indicates a value of 1 3, which is the average number of ethylene oxide group addition moles, (B) 0.8 to 16% by weight of an alkylsulfosuccinate or a polyoxyalkylenealkylsulfosuccinate represented by the following formula (II):

$$R_2-O-(CHCH_2O)_n-\overset{R_3}{\underset{|}{C}}OCHCH_2COOM \qquad (II)$$
$$\phantom{R_2-O-(CHCH_2O)_n-COCH}|SO_3M$$

wherein $R_2$ represents a linear or branched alkyl group of a $C_{8-20}$ carbon atom content, $R_3$ represents a hydrogen atom or a methyl group, M represents an alkali metal, an alkaline earth metal, an ammonium ion, an alkyl group-substituted ammonium with the alkyl group having a $C_{1-3}$ carbon atom content, or a hydroxy alkyl group-substituted ammonium with the hydroxy alkyl group having a $C_{2-3}$ carbon atom content, n is a value of 0 to 8, which is the average number of addition moles, (C) 8 to 24% by weight of a fatty acid dialkanol amide of the following formula (III):

$$R_4\overset{O}{\underset{\|}{C}}-N\overset{\diagup R_5OH}{\underset{\diagdown R_6OH}{}} \qquad (III)$$

wherein $R_4$ represents a linear or branched, saturated or unsaturated hydrocarbon group of a $C_{7-17}$ carbon atom content, and $R_5$ and $R_6$ independently represent a group $-C_2H_4$ or $-C_3H_6$, and (D) 50 to 81% by weight of water; and wherein the ratio of the components (B), (C), and (D) lies within a region defined by straight lines linking the following four points of a three-component trigonometric diagram:
   a'[(B)=10 : (C)=13 : (D)=77],
   b'[(B)=10 : (C)=25 : (D)=65]
   c'[(B)=2 : (C)=25 : (D)=73], and
   d'[(B)=2 : (C)=13 : (D)=85].

2. The pearling agent dispersion of claim 1, wherein the amount of said component (A) ranges from 20–30%, the amount of said component (B) ranges from 1.6–8% by weight and the amount of component (C) ranges from 10.4–20% by weight.

3. The pearling agent dispersion of claim 1, wherein the dispersion has a pH within the range of 4–11.

4. The pearling agent of claim 1, wherein said alkali metal of substituent M is sodium or potassium and said alkaline earth metal is calcium or magnesium.

* * * * *